(12) United States Patent
Ljunggren et al.

(10) Patent No.: US 6,228,990 B1
(45) Date of Patent: May 8, 2001

(54) ESTROGEN RECEPTOR LIGANDS

(75) Inventors: Jan Ljunggren, Solna; Ann-Gerd Thorsell, Stockholm; Owe Engstrom, Nacka; Tomas Bonn, Huddinge; Mats Carlquist, Spanga, all of (SE); Andrzej M. Brzozowski, York (GB); Ashley C. W. Pike, York (GB); Roderick E. Hubbard, York (GB)

(73) Assignee: Kara Bio AB, Huddinge (SE)

( * ) Notice: Subject to any disclaimer, the term of this patent is extended or adjusted under 35 U.S.C. 154(b) by 0 days.

(21) Appl. No.: 09/249,645

(22) Filed: Feb. 12, 1999

(30) Foreign Application Priority Data

Feb. 13, 1998 (GB) .................................................. 9803062

(51) Int. Cl.⁷ .................................................. C07K 17/00
(52) U.S. Cl. ........................................... 530/350; 530/412
(58) Field of Search ...................................... 530/350, 412

(56) References Cited

PUBLICATIONS

Pike et al. "Structure of the ligand–binding domain oestrogenreceptor beta in the presence of a partial agonist and a full antagonist" EMBO J. 18 (17), 4608–4618, Sep. 1999.*
Shiau et al. "The structure bases of estrogen receptor/coactivatir . . . " Cell 95, 927–937, Dec. 1998.*
Tanenbaum et al. "Crystallographic comparison of esterogen and progestrone . . . " Proc. Natl. Acad. Sci. USA, 95, 5998–6003, May 1998.*

* cited by examiner

*Primary Examiner*—Nashaat T. Nashed
(74) *Attorney, Agent, or Firm*—Todd E. Garabedian; Wiggin & Dana

(57) ABSTRACT

The application relates to a crystal comprising at least 150 amino acid residues of the estrogen receptor-β (ERβ) ligand binding domain complexed with a ligand which is an antagonist or a partial agonist.

15 Claims, 13 Drawing Sheets

ER-beta/genistein complex

ER-beta/genistein complex

ER-beta/raloxifene complex

ER-beta/raloxifene complex

ER-beta/KB-177complex

ER-beta/KB-177 complex

Affinity enhancing substituents marked by "R".

Covered by prior art:
hydrophobic substituents
α-face: 7α, 14α, 16α, and 17α
β-face: 11β

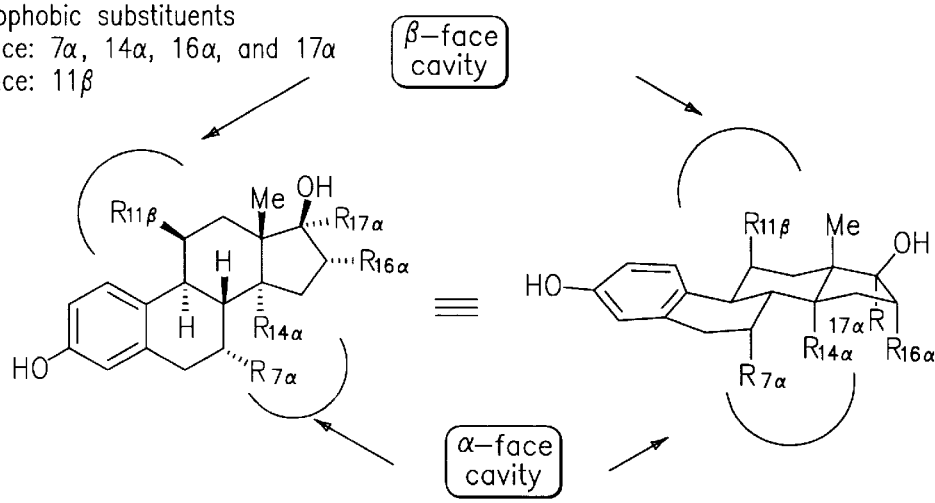

Prior art reviewed in "The estradiol pharmacophore: ligand structure—estrogen receptor binding affinity relationships" G.M. Anstead, K.E. Carlson, and J.A. Katzenellenbogen, Steroids, 62(3):268–303 (1997).

*FIG. 5a*

Affinity enhancing substituents marked by "R".

Not covered by prior art:
hydrophobic substituents
α-face: 9α and 12α
β-face: 8β, 15β, and 18

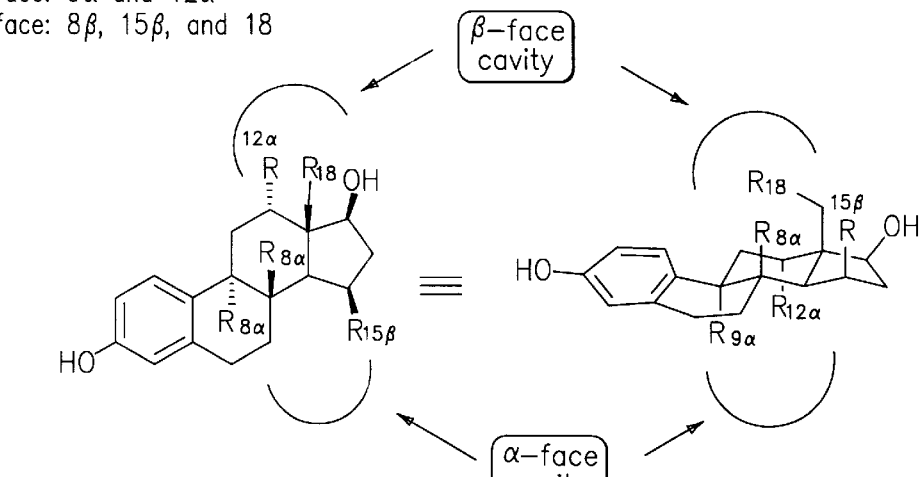

R = Me, Et, i-Pr
fluorinated Me, Et, and i-Pr
Cl, Br, and I

*FIG. 5b*

Affinity enhancing substituents marked by "R".

Affinity enhancing substituents. Replacement of 4'-OH group in raloxifene with 4'-NH₂ provides the opportunity of picking up an additional hydrogen bond to His-524.

Guanidino affinity enhancing substituent at position-3 of the steroid nucleus and position-6 of the benzothiophene nucleus.

Selectivity enhancing substituents $R_3$, $R_2'$, $R_3'$, and $R_6'$.

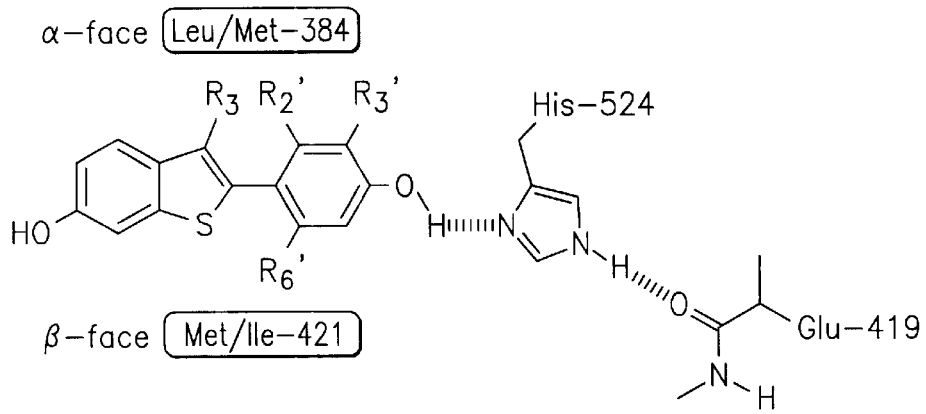

$R_3$, $R_2'$, $R_3'$, and $R_6'$ = Cl, Br, I, Me, Et, $i$-Pr, and perfluoro Me, Et, and $i$-Pr.

Selectivity enhancing substituents $R_3$, $R_2'$, $R_3'$, and $R_6'$. Movement of hydroxyl from position-4' to -5' biases binding orientation and therefore further enhances selectivity

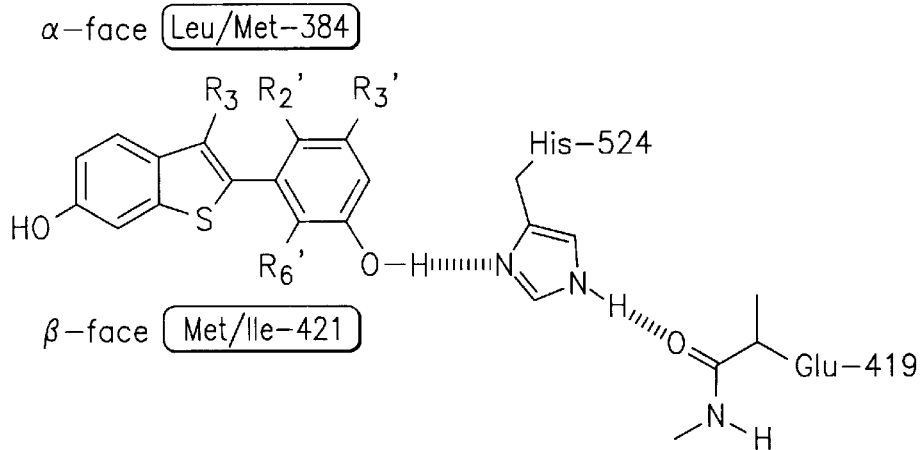

$R_3$, $R_2'$, $R_3'$, and $R_6'$ = Cl, Br, I, Me, Et, $i$-Pr, and perfluoro Me, Et, and $i$-Pr.

*FIG. 6b*

Selectivity enhancing substituents $R_3$.

modeling suggests that benzyl group of NRB−03855 may form a "π−teeing" interaction with Phe−445 and not with Tyr−445 which may account for the observed α−selectivity

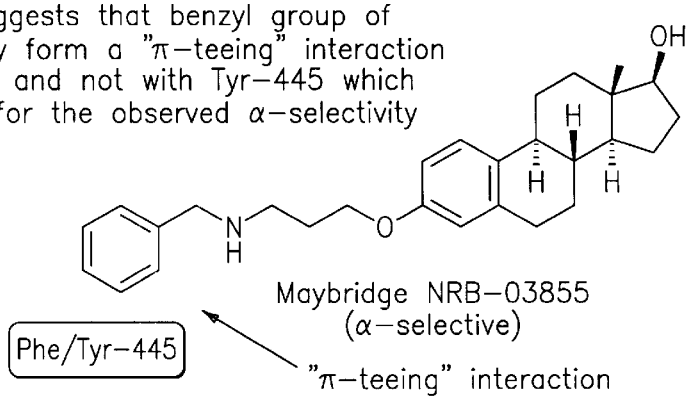

Maybridge NRB−03855 (α−selective)

Phe/Tyr−445

"π−teeing" interaction

*FIG. 6c*

Selectivity enhancing substituents $R_6$.

"water channel" may be reached from 6−position

Ile/Val−326 conserved Glu−323

Phe/Tyr−445

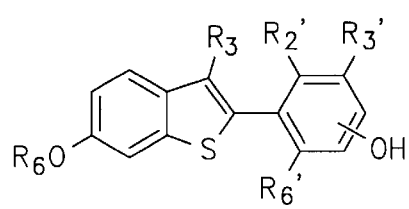

Phe/Tyr−445 may be reached with R−$(CH_2)_n$−chain where n=4, 5, or 6 and R=aromatic or heteroaromatic ring.

*FIG. 6d*

Selectivity enhancement reinforced by charged assisted hydrogen bond between substituent "R" in the ligand and either Glu-323 or Lys-449 in the receptor.

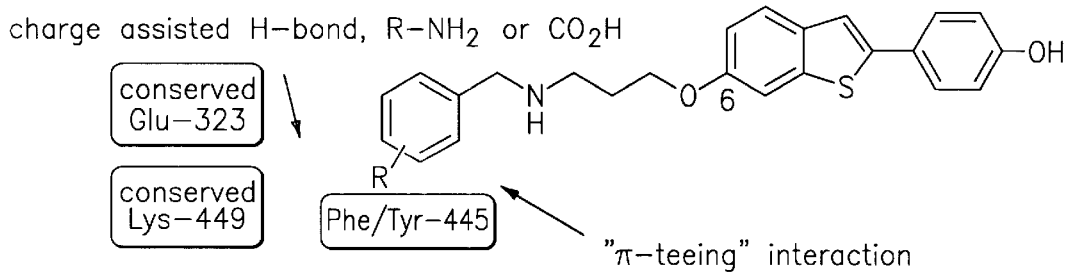

Increasing α-selectivity by reinforcing Phe-445 interaction with H-bonding to Glu-323

FIG. 6e

Selectivity enhancement reinforced by hydrogen bond network between pyridone ring in the ligand and residues Glu-323 and Lys-449 in the receptor

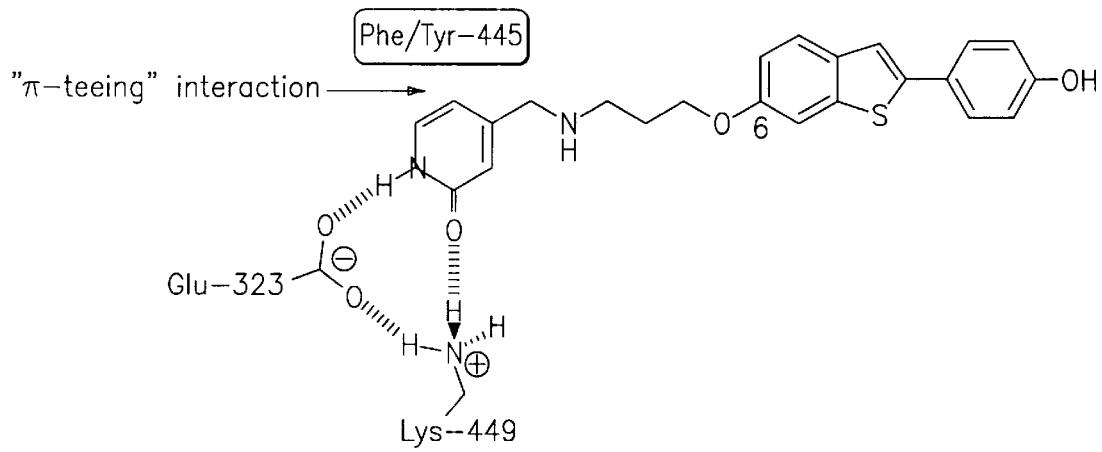

FIG. 6f

ESTROGEN RECEPTOR LIGANDS

BACKGROUND OF THE INVENTION

1. Field of the Invention

This invention relates to estrogen receptors and ligands for them, and in particular to crystalline estrogen β receptor (ERβ) and to methods of identifying ligands utilizing crystalline ERβ.

2. Brief Description of the Art

The thyroid hormone receptor (TR) is known and its three-dimensional structure, and hence its ligand binding domain, has been determined. Knowledge of the three-dimensional structure has enabled a better understanding of the modes of ligand binding and the determination of the optimum conformation of ligand to bind to the receptor. It is generally believed in the art that the TR structure also provides a guide to the design of ER ligands.

Estrogen steroid hormone and thus the estrogen receptor (ER) is a member of the steroid hormone receptor family. Its primary natural ligand is estradiol (E2). However, it is known that a large number of structurally diverse non-steroidal compounds such as raloxifene, centchroman, coumestrol, diethylstilbesterol, esculin, tamoxifen, zearalenone, and zindoxifen also bind to the estrogen receptor (FIG. 4). The majority of these non-steroidal estrogen receptor ligands contain 2–4 carboxylic, aromatic, and/or heterocyclic rings connected by a 1–3 atom chain. One or more of the rings may be fused with the central atom chain or with each other.

It has been proposed that the receptor possesses a multi-functional modular structure potentially having discrete domains for DNA binding, ligand binding, and transactivation. The ligand binding domain (LBD) has been designated domain E and is the largest domain of the estrogen receptor. The ligand binding domain includes a ligand recognition site and regions for receptor dimerization interaction with heat shock proteins, nuclear localization and ligand dependent transactivation.

A review of the structure and functioning of the estrogen receptor is provided in an article by Katzenellenbogen, J. et al., *Steroids*, (1997) 62(3):268–303.

It is known that compounds which bind to the estrogen receptor are potentially useful in the treatment of a wide range of disease states. These include estrogen agonists for treatment of disease linked to estrogen deficiency (e.g. osteoporosis, cardiovascular and neurodegenerative diseases in post menopausal women) and estrogen antagonists for treatment of breast and uterine cancer. Furthermore, it is known that certain ligands such as tamoxifen display mixed agonist/antagonist action (that is they are either estrogen agonists, estrogen antagonists, or a partial estrogen antagonists when binding to the estrogen receptors of different tissues) and such compounds may simultaneously prevent bone loss and reduce the risk of breast cancer. It is further known that benzothiophenes are usable as agonists or antagonists to steroid hormones, and that it is possible to modify their binding mechanics, for example the binding affinity, by changing the substituent groups at various positions on the molecule. Therefore, it would be desirable to be able to design ligands which are recognizable by and able to bind to the estrogen receptor. Additionally, it would be desirable to know the three dimensional structure of the estrogen receptor. Such knowledge would be useful for the design of compounds intended to bind to the estrogen receptor. The present inventors have been able to produce an estrogen receptor crystal and to determine from that the three dimensional structure of the estrogen receptor. Unexpectedly, the thus determined ER structure reveals that the TR structure does not provide a good model for binding of ligands to ER.

Our copending patent application No. PCT/GB98/01708 discloses inter alia, the crystal co-ordinates of crystalline estrogen receptor alpha (ERα).

SUMMARY OF THE INVENTION

We have now succeeded in crystallizing ERβ bound to a ligand which is an antagonist or partial agonist and determining its crystallographic co-ordinates. Therefore, in a first aspect the present invention provides a crystal comprising at least 150 amino acid residues of the ERβ ligand binding domain complexed with a ligand which is an antagonist or a partial agonist.

In a second aspect, the present invention provides ligands, particularly synthetic ligands, of ERβ identified by use of such a crystal.

In a third aspect of the invention, methods for designing ligands which will bind to ERβ are provided. Such methods use three dimensional models based on the crystals of the estrogen receptor ligand complex. Generally, such methods comprise determining compounds which are likely to bind to the receptor based on their three dimensional shape compared to that of the ERβ and in particular the ligand binding domain of the ERβ. Preferably, those compounds have a structure which is complementary to that of the ERβ. Such methods comprise the steps of determining which amino acid or amino acids of the ligand binding domain of the ERβ interacts with the binding ligand, and selecting compounds or modifying existing compounds, to improve the interaction. Preferably, improvements in the interaction are manifested as increases in the binding affinity but may also include increases receptor selectivity and/or modulation of efficacy.

Preferably the ligands bind to the ERβ with a high binding affinity, for example within the range of 20–2000 pmol.

The ligands may bind tightly to the ERβ yet not up-regulate gene expression thereby inhibiting the action of estradiol and estradiol mimetics. Thus, the invention also provides a method of inhibiting the activity of estradiol or estradiol mimetics by providing ligands which bind to ERβ with a high affinity, blocking the activity of estrogens. Alternatively, binding of the ligand to the ERβ may cause conformational changes to the ERβ inhibiting further binding thereto. The invention further provides a method of inhibit estradiol activity in an animal, the method comprising administering to the animal a ligand which binds to at least the LBD, of the ERβ with high affinity and blocks binding of further ligands to at least the LBD of the ERβ. Such ligands are useful in for example, the treatment of estrogen receptor mediated diseases in females.

BRIEF DESCRIPTION OF THE DRAWINGS

Embodiments of the invention will now be described in more detail, by way of example only, with reference to the accompanying drawings FIGS. 1 to 6 of which:

FIGS. 5a, 5b and 5c show modifications made to the steroid nucleus of ligands which bind to the estrogen receptor;

FIGS. 5d, 5e and 5f show how affinity of the ligand can be enhanced by adding substituents; and FIGS. 6a–6f show selectivity enhancement by using different substituents on the estrogen receptor ligand.

DETAILED DESCRIPTION OF THE INVENTION

Structure Based Design of ER Ligands

Figure 1A:
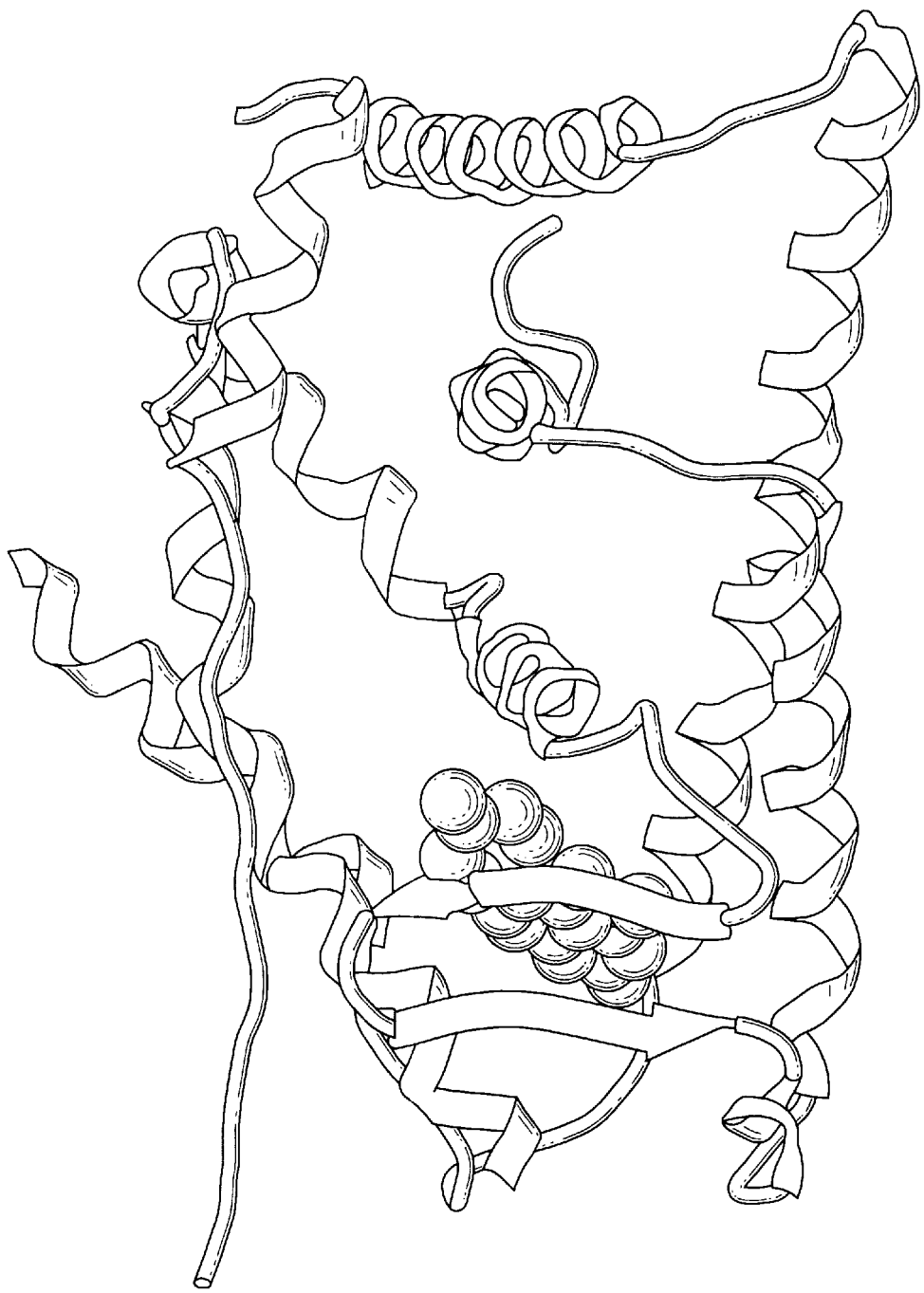
FIG. 1 shows orthogonal views (a and b) of the crystallographic structure of the ligand binding domain of the estrogen receptor beta isoform complexed with genistein. The secondary structure of the receptor is represented by ribbons (alpha helices), ribbons with arrows (beta pleated sheets), and tubes (loops and random coils). The ligand genistein is depicted as a space filling CPK model.
Figure 1B:
Figure 2A:
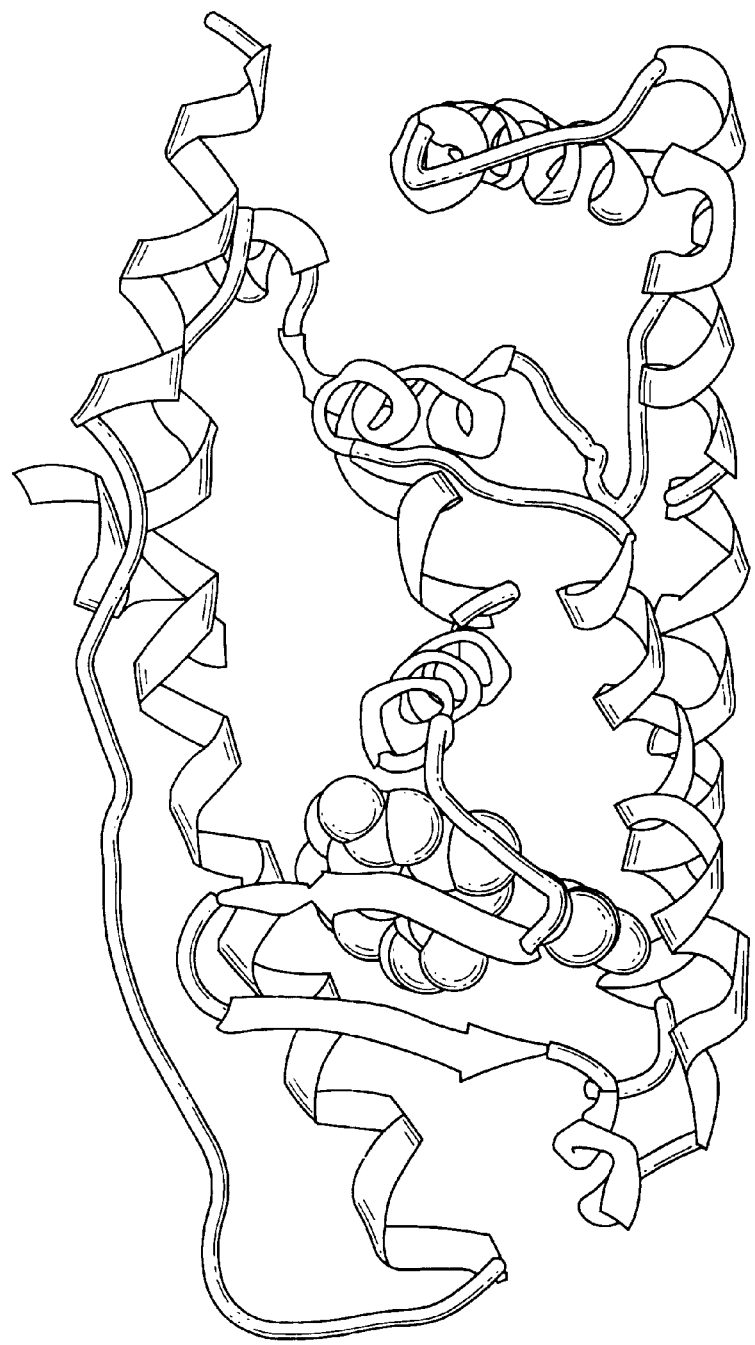
FIG. 2 shows orthogonal views (a and b) of the crystallographic structure of the ligand binding domain of the estrogen receptor beta isoform complexed with raloxifene. The structure of the receptor and ligand are depicted as in FIG. 1.
Figure 2B:
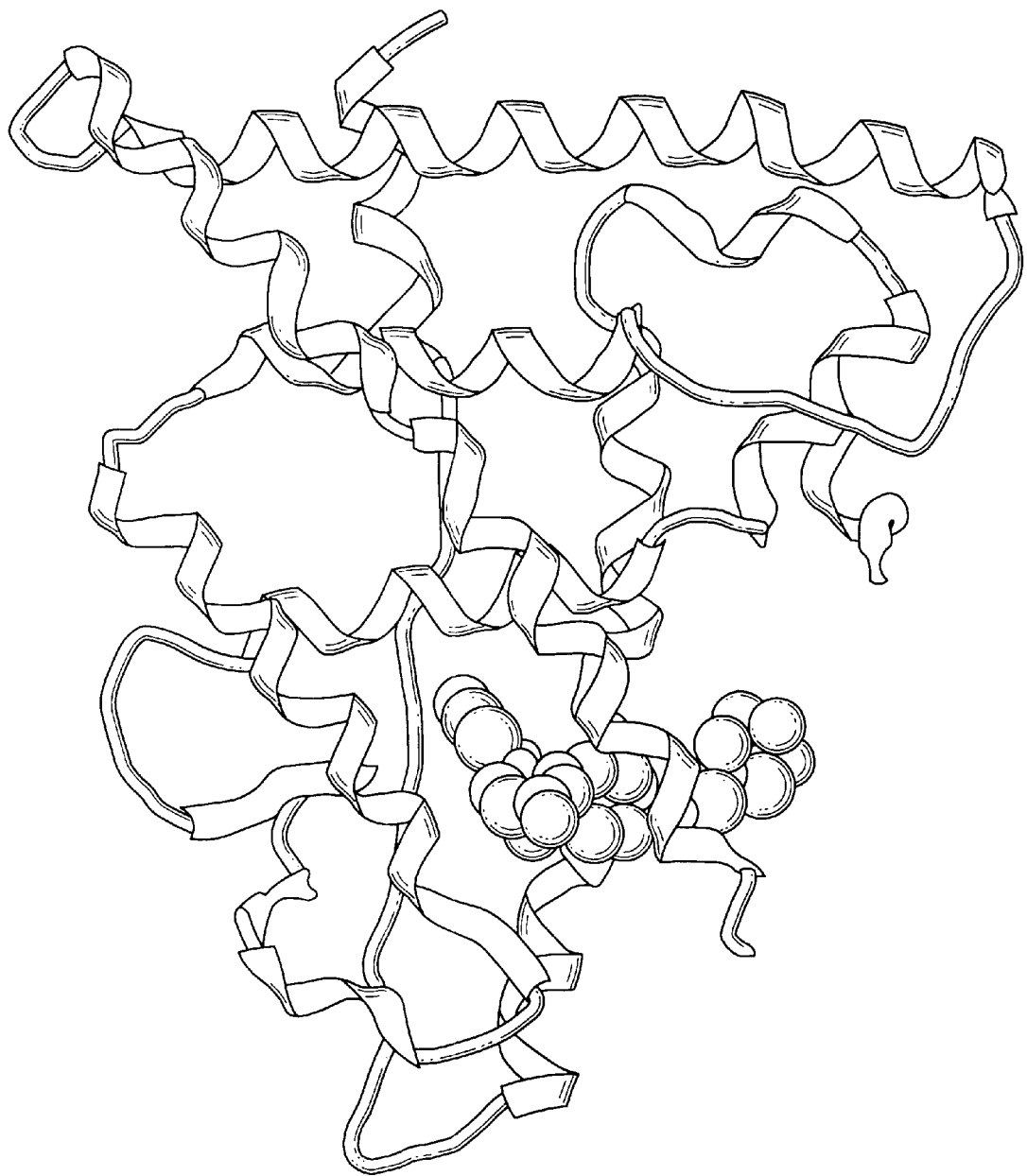
Figure 3A:
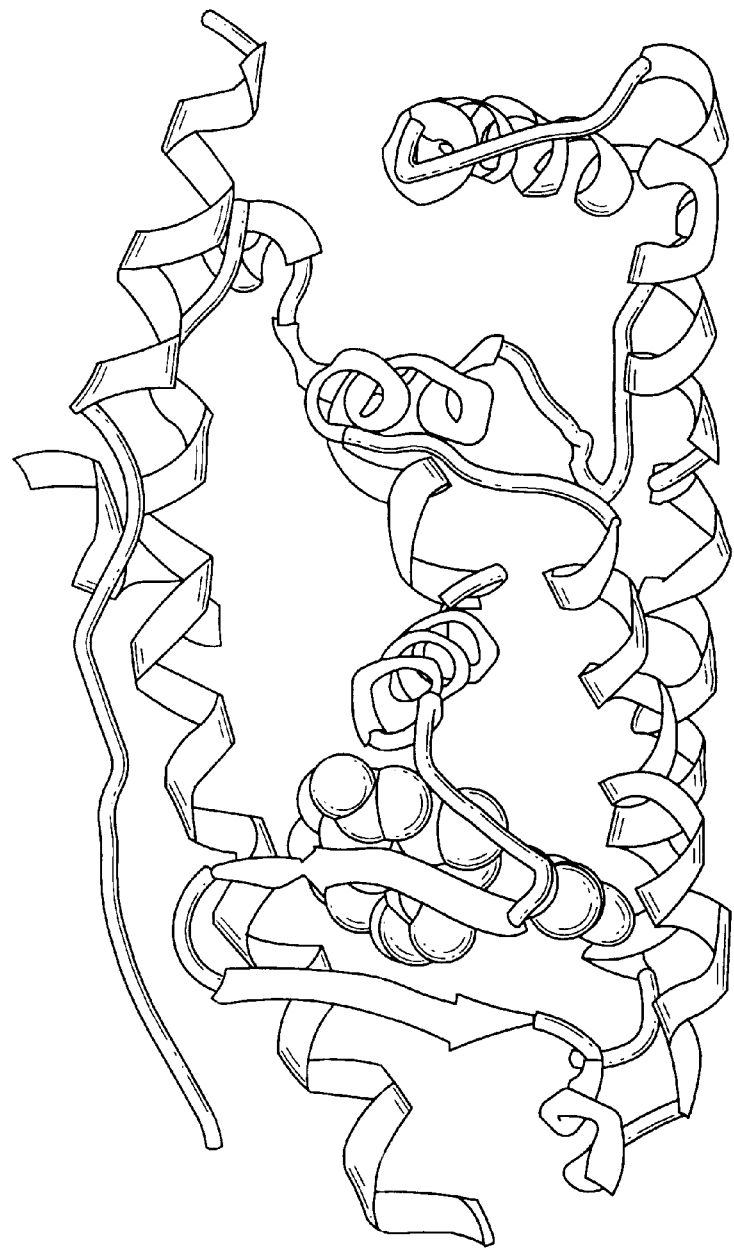
FIG. 3 shows orthogonal views (a and b) of the crystallographic structure of the ligand binding domain of the estrogen receptor beta isoform complexed with KB-177 ([2-(4-hydroxyphenyl)-6-hydroxybenzo[beta]thienyl-3-yl][4-carboxyphenyl]methanone). The structure of the receptor and ligand are depicted as in FIG. 1.
Figure 3B:
Figure 4:
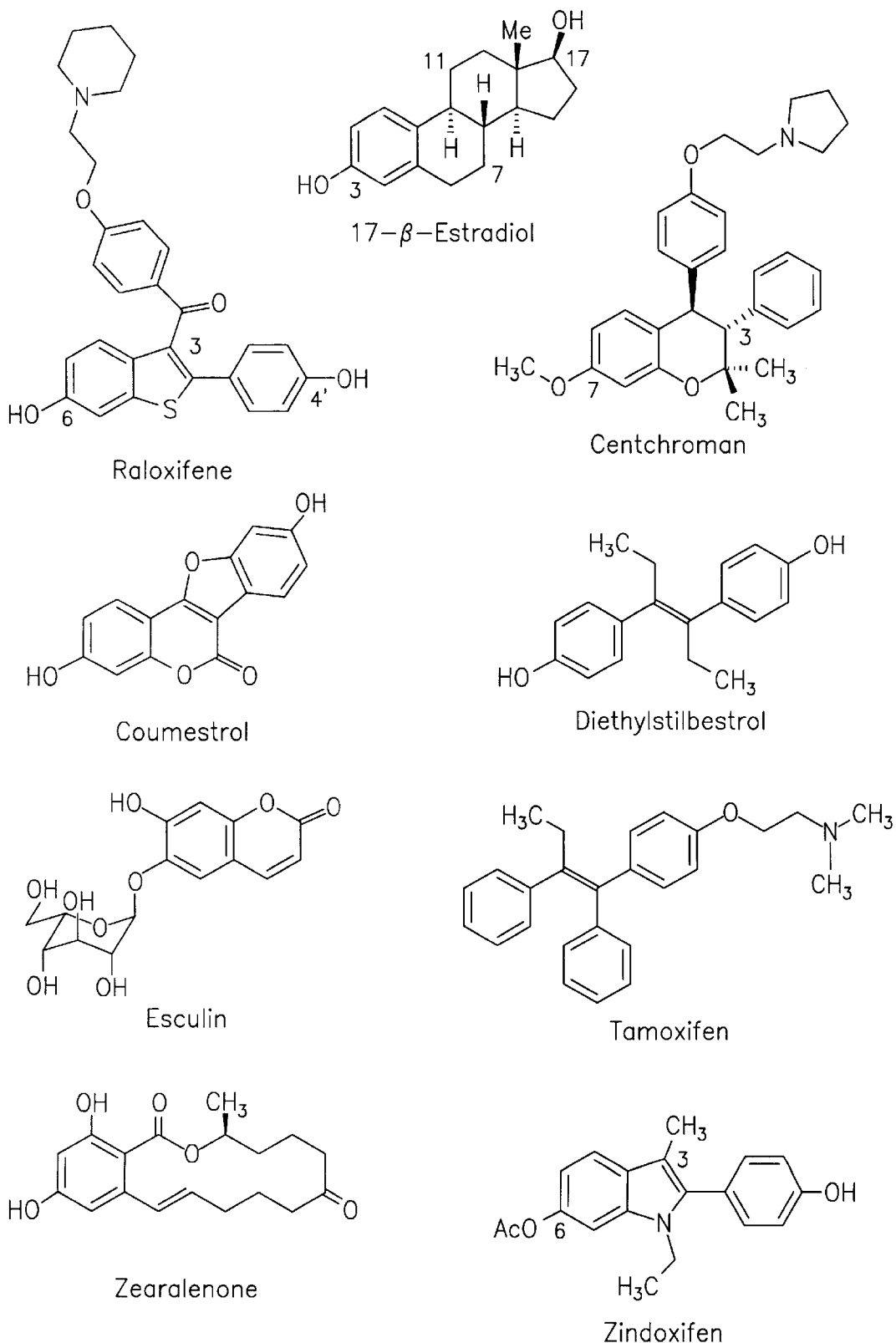
FIG. 4 shows the structure of several representative estrogen receptor ligands.

The present work has elucidated the structure of the ligand binding cavity of ERβ. Knowledge of the structure of this cavity has utility in the design of structurally novel ERβ ligands and in the design of non-obvious analogs of known ERβ ligands with improved properties. These enhanced properties include one or more of the following: (1) higher affinity, (2) improved selectivity for either the α- or β-isoform of the ER, and/or (3) a designed degree of efficacy (agonism vs. partial agonism vs. antagonism). Without knowledge of the ERβ structure, modifications to produce ligands with enhanced properties and a reasonable likelihood of success would not be available to those skilled in the art. The ERβ structure also has utility in the discovery of new, structurally novel classes of ERβ ligands. Electronic screening of large, structurally diverse compound libraries such as the Available Chemical Directory (ACD) will identify new structural classes of ERβ ligands which will bind to the 3-dimensional structure of the estrogen receptor. Additionally the ERβ structure allows for "reverse-engineering" or "de novo design" of compounds to bind to ERβ. This work is also described in copending British Application No. GB 9803062.0 which is herein incorporated by reference in its entirety.

(1) Enhanced Affinity

The present work has revealed the presence of estrogen receptor beta defined β- and α-face cavities centered respectively above and below the B- and C-rings of genistein.

The present invention provides new ligands which exploit this discovery by filling the α- and β-face cavities.

Preferably, the ligand fills at least one of the α- and β-face cavities so as to exclude water from the cavity or cavities.

The ligands produced in accordance with the invention bind more effectively to the ERβ than genistein. The ligand may bind with twice the binding affinity of genistein, preferably three times the affinity, and most preferably ten or more times the affinity.

Modifications to the steroid nucleus may be made at the positions marked in R in FIG. 8a and 8b (α-substitution at the 7-, 9-, 12-, 14-, 16-, and 17-positions; β-substitution at the 8-, 11-, 15-, and 18-positions). Preferably, those substituents are hydrophobic substituents, e.g., methyl, ethyl, iso-propyl, chlorine, bromine, or iodine.

Modifications to 2-aryl benzothiphenes may be made at the 2'-, 3'-, and 6'-positions (FIG. 5C) in order to fill the α- and β-face cavities of ER. Preferably substituents should be present in at least two of the following three positions: 3, 2', or 6' so that a perpendicular conformation between the B- and C-rings of the 2-aryl benzothiophene nucleus is enforced. This perpendicular conformation facilitates the positioning of the 2'-, 3'-, and 6'-substituents in the α- and β-face cavities of the ERβ.

In a manner analogous to the benzothiophene series, the affinity of other classes of non-steroidal ERβ ligands may be enhanced by substitution of small hydrophobic substituents at positions marked $R_2'$, $R_3'$, and/or $R_6'$ in FIG. 8C.

Preferably, the ligand produce in accordance with the invention fills at least one of the α- and β-cavities of the ERβ without perturbing the remainder of the ERβ structure.

Another aspect of this invention reveals an unfilled hydrophobic cavity in the raloxifene/ERβ complex. Filling this cavity with hydrophobic substituents so as to exclude water will enhance binding affinity. This cavity may be filled by positioning a hydrophobic substituent on the ethoxyphenyl sidechainα to the piperidinyl nitrogen atom of raloxifene. This hydrophobic substituent may be a linear alkyl or perfluoralkyl group ($-CH_3$ to $-C_{10}H_{21}$, $-CF_3$ to $-C_{10}F_{21}$), benzyl ($-CH_2Ph$), or methylene cyclohexyl ($-CH_2C_6H_{11}$).

In a third aspect of this invention, examination of the ERβ structure reveals that the hydroxyl group at position-3 of estradiol or position-6 of raloxifene form hydrogen bonding interactions with Glu-353 and Arg-394 (FIG. 5a and 5b). It is known that replacement of the hydroxyl group at position-3 of estrodiol or position-6 of raloxifene results in a decrease in affinity for the ERβ. The invention reveals the reason for this reduction in affinity: while one of the hydrogen atoms of the amino group forms a favourable hydrogen bonding interaction with Glu-353, the second hydrogen atom forms an unfavourable electrostatic interaction with Arg-394. Furthermore this invention reveals a method for enhancing the affinity of 3-amino analogs of estradiol and 6-amino analogs of raloxifene: replacement of one of the two hydrogen atoms of the amino group with an alkyl group to produce a secondary amino group. Alternatively, the group may be replaced with a guanidino group (FIG. 5e) which will pick up two additional hydrogen bonding interaction, the first is a salt bridge to Glu-353 and the second is a hydrogen bonding interaction with a backbone carbonyl group in residue Leu-387. Similar enhancement of affinity for the ERβ may be achieved by replacement of the guandino group with a fused 2-aminopyrrole (FIG. 5).

In a closely related aspect of this invention, an understanding is provided for the reduction in affinity for the ERβ seen in ether derivatives at either position-3 of estradiol or position-6 of raloxifene: electrostatic repulsion between the ether oxygen atom of the ligand and Glu-353 in the ERβ. This invention reveals a way of increasing the affinity of estradiol position-3 or raloxifene position-6 ether derivatives: replacement of the ether oxygen atom with an amino (NH) group.

Figure 5C:
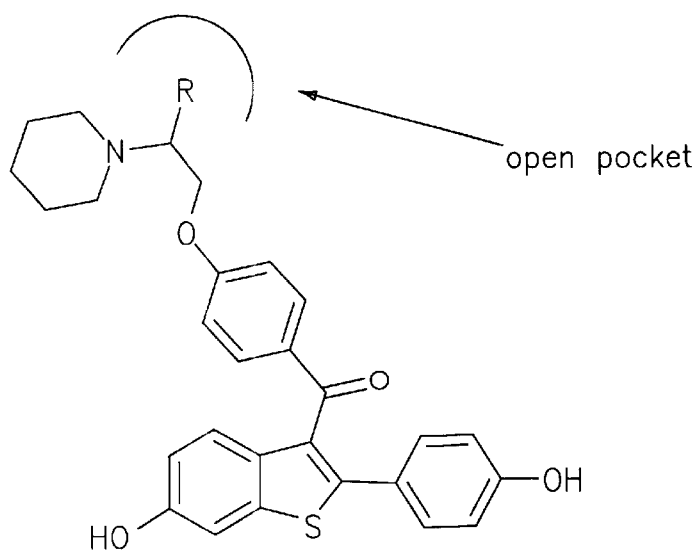
Figure 5D:
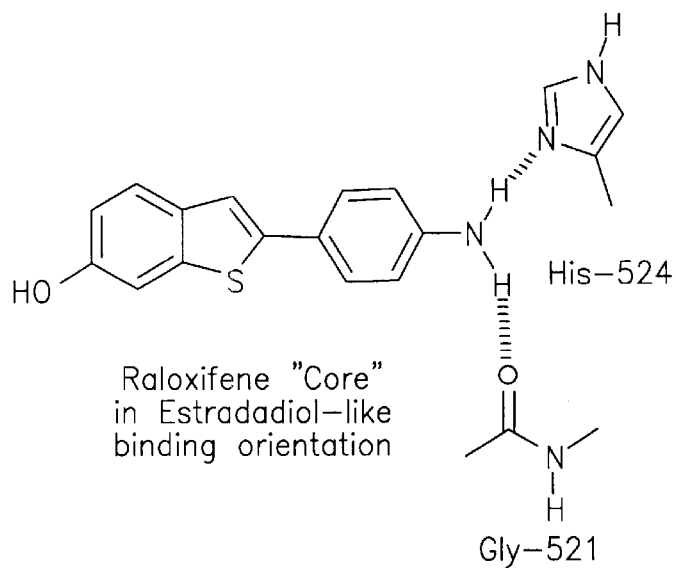
Figure 5E:
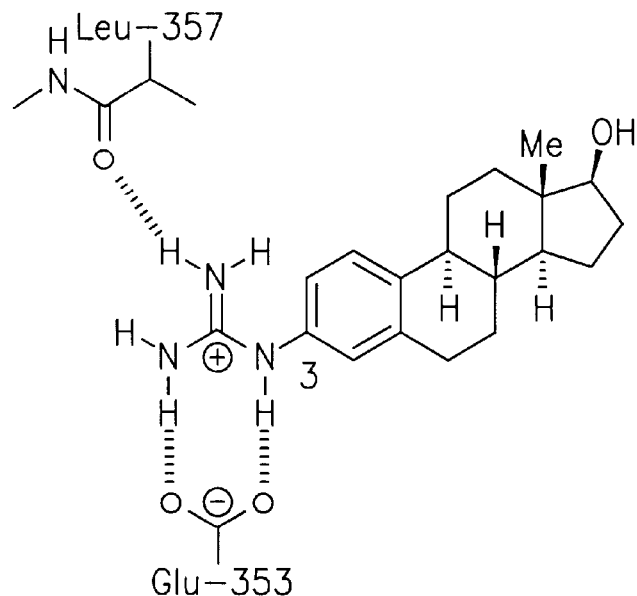
Figure 5E:
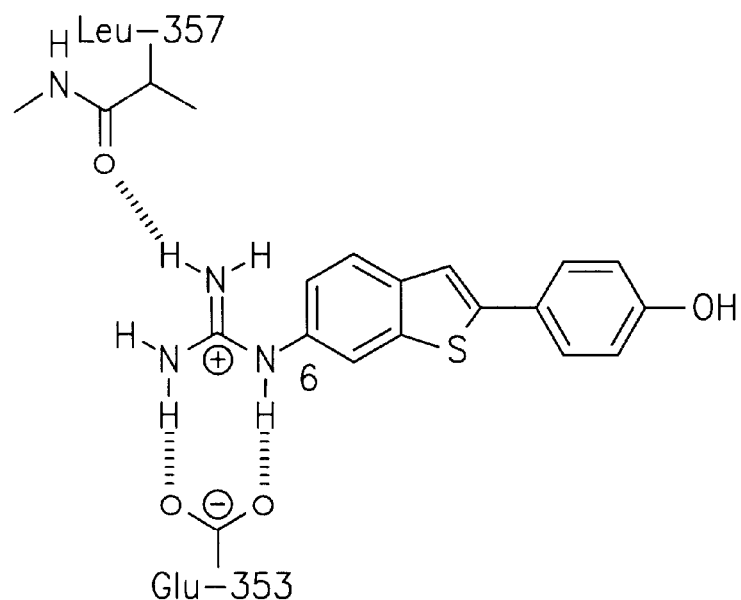

In a fourth aspect of this invention, replacement of the 4-hydroxyl group of raloxifene will enhance affinity by picking up a second hydrogen bonding interaction between the amino group and a backbone carbonyl group in Gly-521 of the ERβ (FIG. 5d).

(2) Improved Selectivity

The estrogen receptor has been found to have two discrete forms, known as ERα and ERβ. Furthermore the ratio of the α- to the β-forms of the ER may vary considerably in different cell and tissue types. Therefore it may be possible to dissociate desirable therapeutic effects from undesirable side effects of estrogen receptor ligands by designing ligands that selectively bind to one or the other isoforms of the estrogen receptor.

The α- and β-forms of the estrogen receptor differ significantly in their primary sequence and slightly in their tertiary structure. As a consequence of these receptor differences, ligands may bind with different affinity to the two isoforms.

The present inventors have been able to isolate, differentiate and produce crystals for both the ERα and ERβ. The present invention is confined however to ERβ. Further, the differences between the ERα and ERβ has been determined and using these differences, the ability of a ligand to bind to either the ERα and ERβ receptors or to both receptors can be predicted. Hence, if it is known that one tissue possesses solely one form of the estrogen receptor, then it is possible to confer a degree of tissue specificity to a ligand by designing the ligand to bind to that predominant form of the receptor. Advantageously, ligands may be designed to specifically bind ERα or ERβ.

Furthermore, a detailed understanding of the different receptors enables the different behavior of a compound in different tissues to be understood, for example the estrogenic or anti-estrogenic behavior of raloxifen (RAL) dependence on the tissue in which it is active.

Thus, in a further aspect, the invention provides estrogen receptor ligand binding domain crystals for ERβ. Specificity of ligands for either the ERα and ERβ or even to a specific ratio of ERα to ERβ is also provided. The advantage of this is that tissue specificity is conferred to the ligand. Thus, the invention also provides ligands, particularly synthetic ligands for ERβ together with methods for their design.

The present invention provides new ligands which exploit these differences by positioning ligand substituents in close proximity to one or more amino acid residue that differ between the α- and β-isoforms of the ER.

The ligands produced in accordance with the invention bind more effectively to either the α- or β-isoforms of the ER. The selectivity of the binding between the α- or β-isoforms may be ten-fold, more preferably one hundred-fold, and most preferably greater than one thousand-fold.

For example, in the β-face cavity of ER-α, the amino acid residue at position-384 is Leu (sidechain volume=76.6 Å$^3$) whereas in the corresponding position-293 of ER-β, the amino acid residue is Met (sidechain volume=79.3 Å$^3$). Therefore the β-face cavity of ER-β is smaller. Consequently ER-α selectivity may be enhanced by positioning substituents larger than a methyl group in the β-face cavity in close proximity to residue-384. Interaction between the ligand and residue-384 may be enhanced by introducing substituents at the β 8-, 15-, or 18-positions on the steroid nucleus.

In the α-face cavity of ER-α, the amino acid residue at position-421 is Met (sidechain volume=79.3 Å$^3$) whereas in ER-β, it is Ile-330 (sidechain volume=77.3 Å$^3$). Therefore the α-face cavity of ER-α is smaller. This difference may be exploited to produce β-selective compounds through substitutions larger than a methyl group at the α 14-, 16-, or 17-positions of the steroid nucleus.

Similarly, substitutions may be made from either the 2'- or 3'-positions of the 2-arylbenzothiophene nucleus to interact with residue-384 in the β-face cavity or from the 6'-position to interact with residue-421 in the α-face cavity (FIG. 6a and 6b). However free rotation about the C2-C1' bond will effectively interchange the substituents at the 2'- and 6'-positions thereby reducing selectivity. Moving the hydroxyl group from position-4' (FIG. 6a) to position-5' (FIG. 6b) will bias the binding orientation such that the R$_2$' substituent will be positioned in the β-face pocket and the R$_6$ substituent in the α-face pocket. This bias results from the fact that only one of the two possible rotamers about the C2-C1' bond will allow hydrogen bond formation between the 5'-hydroxyl group and the receptor residue His-524.

This invention also provides a means of enhancing the selectivity of other classes of non-steroidal ER-β ligands. In a manner analogous to the benzothiophene series of ER-β ligands, substituents larger than methyl may be introduced at either the R$_2$' or R$_3$' positions to produced ER-α selective compounds or at R$_6$' to produce ER-β selective compounds (FIG. 5c).

Substitutions may be made from position-3 of the steroid nucleus or position-6 of the benzothiophene nucleus to exploit the differences between ER-α and ER-β at position-326 (Ile in ER-α and Val in ER-β) and at position-445 (Phe in ER-α and Tyr in ER-β).

(3) Modulation of Efficacy

This invention provides an understanding of the differences between estrogen and antiestrogen binding and therefore a means to design ER-β ligands with the desired degree of efficacy. An examination of the differences between the ER-β/genistein and ER-β/raloxifene complexes reveals a large movement in Helix-12 (H12). H12 adopts an "agonistic" conformation defined by the structure of the ER-β/genistein complex and an "antagonistic" conformation defined by the structure of the ER-β/raloxifene complex. These two conformation are in thermodynamic equilibrium. When the ER-β is complexed with a full agonist, such as genistein, the equilibrium lies far in the direction of the "agonistic" conformation. In contrast, while when complexed with an antagonist, the equilibrium is pushed in the direction of the "antagonistic" conformation. In the case of raloxifene, the large sidechain at position-3 sterically collides with H12 in it's agonistic conformation, thereby driving the equilibrium strongly in the antagonistic direction. By introduction of progressively shorter sidechains at position-3 of raloxifene, the equilibrium will be gradually shifted back towards the agonist conformation. Thus, this invention provides a means of developing ligands with the desired degree of efficacy (agonist, partial agonist, or antagonist).

In particular, the importance of H12 has been determined as playing a central role in determining the efficacy (agonism vs. antagonism) of a ligand. Thus, ligands which are able to bind to and/or alter the conformation of H12 are of particular importance when designing a ligand or assessing the binding of a ligand, for the estrogen receptor.

The present inventors have also found the reason why raloxifene has a different binding conformation to that of estradiol, the distinction lying in its active conformation but being unpredictable by virtue of it antagonistic action. The antagonism has been shown, by the present inventors, to be caused by a protruding portion on the raloxifene molecule which causes a large displacement of H12 relative to its conformation in the ER-β/estradiol complex.

Additionally, it has been found that at least the majority of such receptor proteins are in the form a dimer. Such dimerization leads to a potential route for disruption. Disruptions of this type can be used to predict antagonism or to produce antagonists. Disruptions may take the form of ligand binding which alters the conformation of the helices that comprise the dimerization interface or direct binding to the dimerization interface which then inhibits dimerization.

Further, the orientation of the ligand may be keyed to the receptor, in the dimeric or monomeric form. Furthermore, using the crystals of the present invention, the influence of ligand binding to the LBD on the receptor conformation can now be shown to have influences on the behavior of the receptor since it may disrupt the binding of co-activator, co-repressor, or heat-shock proteins. Previously, such predictions could not me made.

Production of estrogen receptor crystals and their application.

The present inventors have been able to isolate, differentiate and produce crystals for both the ER-α and ER-β receptors. The present invention however, is confined to ER-β. Further, the differences between the ER-α and ER-β receptors has been determined and, using these differences, the ability of a ligand to bind to either the ER-α and the ER-β receptor or to both receptors can be predicted. Hence if it is known that one tissue possesses predominately one isoform of the estrogen receptor, then it is possible to confer a degree of tissue specificity to a ligand by designing the ligand to bind to that predominant isoform of the receptor.

Furthermore, a detailed understanding of the different receptors enables the different behavior of a compound in different tissues to be understood, for example the estrogenic or anti-estrogenic behavior of raloxifene (RAL) in dependence on the tissue in which it is active.

Preferably, the crystal is produced from a sequence comprising at least one hundred and fifty amino acids, and preferably at least two hundred amino acids of ER-β. Preferably, the sequence comprises at least a portion of the ligand binding domain of ER-β. More preferably, the sequence comprises the whole ligand binding domain of ER-β.

Preferably, the crystals used can withstand exposure to X-ray, beams used to produce the diffraction pattern data necessary to solve the X-ray crystallographic structure. For example, crystals grown using estrogen receptor sequence bound to a various of ER-β ligands have been found to decompose during exposure to X-ray beams at room temperature, whereas crystals grown using estrogen receptor sequence bound to various ER-β ligands are freezable and are able to withstand exposure to X-ray beams.

Advantageously, the crystals have a resolution determined by X-ray crystallography of less than 3.5 Å and most preferably less than 2.8 Å. Preferably crystals grown using naturally occurring estradiol have an effective resolution of lower than 3.1 Å and crystals grown using raloxifene have an effective resolution of lower than 2.6 Å.

The production of such crystals has enabled the three dimensional structure of the ligand binding domain of ER-β to be mapped. Use of such crystals in conjunction with the map enables a better understanding of how estradiol and other estrogen bind to ER-β with precision. This technique can also enable the design of isoform selective estrogen agonists and antagonists since now the precise differences in the binding sites between ER-α and ER-β are now known.

For example, it was previously proposed that the amino acid residue Phe-425 in ER-α and the corresponding residue Phe-334 in ER-β which both line the ligand binding cavity adopt similar conformations and therefore ligands that probe this region of the receptor would not expected to be isoform selective. However a comparison of the human ER-α/raloxifene vs. rat ER-β/raloxifene complexes shows that the chi-1 sidechain torsion angle (the N-CA-CB-CG angle) differs markedly between the two structures (−156 vs. −87 resepectively). As a consequence, the ER-α binding cavity is effectively larger compared to the ER-β cavity when bound to antagonists. This suggests that raloxifene analogs which possess 2'- and 3'-substituents should be ER-α isoform selective.

Crystals of the ER-β binding domain can be used as models in methods for the design of synthetic compounds intended to bind to the receptor. Such models show why very slight difference in chemical moieties of a ligand potentially have widely varying binding affinities. Hence, the three dimensional structure of the ligand binding domain can be used a pharmaceutical model for compounds which bind to estrogen receptors.

EXAMPLE 1

Materials

Protein purification and crystallisation of the estrogen receptor (ER-β).

The rat or human ER-LBD-β (210–464) was cloned into the pLEX vector (Invitrogen), with an N-terminal FLAG-peptide (IBI), over expressed in *Escherichia coli* GI 724 under control of the inducible PL promoter. Fermentation was carried out in batch and fed batch (glucose limitation) mode in a defined glucose/salt medium at 30° C. Production of recombinant protein was induced by adding tryptophane to a concentration of 1.2 mM. After 3 hr of induction, cells were harvested by centrifugation, and frozen. Thawed cells, corresponding to 1200 mL fermentation volume were disrupted by a Bead Beater (Biospec, Bartlesville, Okla., USA) homogenizer (6×22 sec., with a 3 min resting time between bursts) in 250 mL 100 mM Tris-HCl (pH 8.0), 300 mM KCl, 10% glycerol, 5 mM EDTA, 4 mM DTT, 0.1 mM PMSF and 210 mL glass beads (212–300 microns) at 0° C. After centrifugation, the supernatant was applied to a column of estradiol-Sepharose Fast Flow, 25 mL, (Greene G. et al Proc Natl Acad Sci USA (1980) 77, 5115–5119). (For the human ER-beta the KCl concentration was increased to 600 mM before the extract was loaded to the column.) The column was first washed with 100 mL 100 mM Tris-HCl (pH 8.0), 300 mM KCl (600 mM KCL for human ER-beta), 10% glycerol, 5 mM EDTA, 0.1 mM PMSF, 2 mM DTT, followed by 150 mL 10 mM Tris-HCl (pH 8.0), (300 mM KCl for the human ER-beta), 2 mM EDTA, 0.1 mM PMSF, 2 mM DTT. In the case of human ER-beta the KCl concentration was lowered to 100 mM prior Cys-modification. Reactive Cys residues were modified by washing the column with 100 mL 30 mM Tris-base, 15 mM iodoacetic acid (100 mM KCL for the human ER-beta) and pH 8.1. Excess reagents was washed out by 100 mL 20 mM Tris-HCl pH 8.0 (and 100 mM KCl for human ER-β) followed by 50 mL 20 mM Tris-HCl, pH 8.0, 10% dimethylformamide (and 100 mM KCl for human ER-beta). The ER-LBD-β was eluted by including 50–75 μM of the desired ligand and 250 mM NaSCN to the last buffer. The fractions containing ER-LBD-β was pooled and concentrated (Centriprep 30, Amicon) to 2 mL. Final purification was achieved using a Bio-Rad 491 preparative PAGE instrument according to the user manual. Using one dilution of the Ornstein/Davies buffer system. The stacking (0.5 cm) and resolving (5.5 cm) gels was 5.6% (acrylamide/bis). The elution buffer was 10 mM Tris-HCl pH 8.0 and the electrophoresis was carried out at 12 W. Fractions containing ER-LBD-β was pooled and concentrated (Centriprep 30) to the desired protein concentration. All buffers contains 0.02% $NaN_3$.

Rat ERβ-Raloxifene (rERβ-R) crystallization (SEQ ID NO:2)

Crystals were grown by vapor diffusion using hanging drop technique at 19° C. Best crystals were obtained using 0.03 M Na acetate buffer pH 4.6, 9% (w/v) PEG 4000, 0.06 M ammonium acetate with the addition of 4% dimethylformamide on top. The optimum size of the drop was achieved by mixing 3.0 μL of protein solution (11 mg/mL) with 1.5 μL of the reservoir solution. Upon analysis, the crystals were found to belong to the space group P4122 and have the unit cell dimensions a=67.9 Å, c=148.62 Å, and α=β=γ=90°.

Rat ERβ-KB-000,177 (rERβ-177) crystallization (SEQ ID NO:2)

Crystals were grown by vapor diffusion using hanging drop technique at 19° C. Best crystals were obtained using 0.03 M Na acetate buffer pH 4.6, 9% (w/v) PEG 4000, 0.06 M ammonium acetate. The optimum size of the drop was achieved by mixing 3.0 μL of protein solution (9.5 mg/mL) with 1.5 μL of the reservoir solution. Upon analysis, the crystals were found to belong to the space group P4122 and have the unit cell dimensions a=67.9 Å, b=67.9 Å, c=148.62 Å, and α=β=γ=90°.

Human ERβ-genistein (hER β-gen) (SEQ ID NO:1)

Crystals were grown by vapor diffusion using hanging drop technique at 19° C. Best crystals were obtained using 100 mM Tris-HCl buffer (pH 8.1). 7% (w/v) PEG 6000, 1.9 M NaCl with the addition of 2.7% iso-propanol on top. The optimum size of the drop was achieved by mixing 1.0 μL of protein solution (7 mg/mL) with 1.0 μL of the reservoir solution. Upon analysis, the crystals were found to belong to the space group P6122 and have the unit cell dimensions a=63.2 Å, b=63.2 Å, c=250.36 Å, α=β=90°, and γ=120°.

Rat ERβ-genistein (rERβ-gen) (crystals).

Crystals were grown by vapor diffusion using hanging drop technique at 19° C. Best crystals were obtained using 100 mM Tris-HCl buffer (pH 8.1), 8–12% (w/v) PEG 6000, 1.8–2.1 M NaCl with the addition of 2.5% iso-propanol on top. The optimum size of the drop was achieved by mixing 1.0 μL of protein solution (9–12 mg/mL) with 1.0 μL of the reservoir solution.

Experimental description of ER binding assay

Affinity for the ER (by displacement of $^3$[H]-estradiol) ws measured using the scintistrip assay[1]. Human estrogen receptor (hER) alpha was extracted from the nuclei from SF9-cells infected with a recombinant baculovirus transfer vector containing the cloned hER genes.[2] The concentration of hER's in the extract was measured as specific $^3$[H]-E2 binding with the G25-assay.[3]

1) Haggblad, J., Carlsson, B., Kivelä, P., Siitari, H., (1995) *Biotechniques* 18, 146–151.
2) Barkhem, T., Carlsson, B., Simons, J., Moller, B., Berkenstam, A., Gustafsson J. A. G., Nilsson, S. (1991) *J. Steroid Biochem. Molec. Biol.* 38, 667–75.
3) Salononsson, M., Carlsson, B., Haggblad, J., (1994) *J. Steroid Biochem. Molec. Biol.* 50, 313–318.

The following pages ive the crystal coordinates for:
(1) ER-LBD-genistein (SEQ ID NO:1);
(2) ER-LBD-Raloxifene (SEQ ID NO:2);
(3) ER-LBD-[2-(4-hydroxyphenyl)-6-hydroxybenzo[beta]thienyl-3-yl][4-carboxyphenyl]methanone (KB 177)(SEQ ID NO:2).

---

What is claimed is:

1. A crystal of ERβ ligand binding domain complexed with raloxifine, said crystal belonging to the space group P4122 and having the unit cell dimensions a=67.9 Å, c=148.62 Å, and α=β=γ=90°, said crystal having the protein sequence of SEQ ID NO:2.

2. The crystal of claim 1, wherein said crystal has a resolution determined by X-ray crystallography of less than 3.5 Å.

3. The crystal of claim 1, comprising a binding pocket defined by the structure coordinates of human ERβ ligand binding domain amino acid residues $Met_{252}$, $Leu_{255}$, $Leu_{258}$, $Ala_{259}$, $Glu_{262}$, $Met_{293}$, $Leu_{296}$, $Met_{297}$, $Leu_{300}$, $Arg_{303}$, $Phe_{313}$, $Ile_{330}$, $Ile_{333}$, $Phe_{334}$, $Leu_{337}$, $Gly_{429}$, $His_{432}$, and $Leu_{433}$.

4. The crystal of claim 1, comprising a binding pocket defined by the structure coordinates of human ERβ ligand binding domain amino acid residues $Met_{252}$, $Leu_{255}$, $Thr_{256}$, $Leu_{258}$, $Ala_{259}$, $Asp_{260}$, $Glu_{262}$, $Leu_{263}$, $Trp_{292}$, $Met_{293}$, $Leu_{296}$, $Met_{297}$, $Gly_{299}$, $Leu_{300}$, $Arg_{303}$, $Phe_{313}$, $Gly_{329}$, $Ile_{330}$, $Ile_{333}$, $Phe_{334}$, $Leu_{337}$, $Lys_{428}$, $Gly_{429}$, $Met_{430}$, $Glu_{431}$, $His_{432}$, $Leu_{433}$, $Leu_{434}$, $Met_{436}$, $Val_{441}$, and $Val_{444}$.

5. A process of preparing a crystal of claim 1, comprising the steps of providing ERβ ligand binding domain complexed with raloxifene, and growing one or more of said crystals by vapor diffusion.

6. A crystal of ERβ ligand binding domain complexed with genestein, said crystal belonging to the space group P6122 and having the unit cell dimensions a=63.2 Å, b=63.2 Å, c=250.36 Å, α=β=90°, and γ=120°, said crystal having the protein sequence of SEQ ID NO:1.

7. The crystal of claim 6, wherein said crystal has a resolution determined by X-ray crystallography of less than 3.5 Å.

8. The crystal of claim 6, comprising a binding pocket defined by the structure coordinates of human ERβ ligand binding domain amino acid residues $Met_{252}$, $Leu_{255}$, $Leu_{258}$, $Ala_{259}$, $Glu_{262}$, $Met_{293}$, $Leu_{296}$, $Met_{297}$, $Leu_{300}$, $Arg_{303}$, $Phe_{313}$, $Ile_{330}$, $Ile_{333}$, $Phe_{334}$, $Leu_{337}$, $Gly_{429}$, $His_{432}$, and $Leu_{433}$.

9. The crystal of claim 6, comprising a binding pocket defined by the structure coordinates of human ERβ ligand binding domain amino acid residues $Met_{252}$, $Leu_{255}$, $Thr_{256}$, $Leu_{258}$, $Ala_{259}$, $Asp_{260}$, $Glu_{262}$, $Leu_{263}$, $Trp_{292}$, $Met_{293}$, $Leu_{296}$, $Met_{297}$, $Gly_{299}$, $Leu_{300}$, $Arg_{303}$, $Phe_{313}$, $Gly_{329}$, $Ile_{330}$, $Ile_{333}$, $Phe_{334}$, $Leu_{337}$, $Lys_{428}$, $Gly_{429}$, $Met_{430}$, $Glu_{431}$, $His_{432}$, $Leu_{433}$, $Leu_{434}$, $Met_{436}$, $Val_{441}$, and $Val_{444}$.

10. A process of preparing a crystal of claim 6, comprising the steps of providing ERβ ligand binding domain complexed with genestein, and growing one or more of said crystals by vapor diffusion.

11. A crystal of ERβ ligand binding domain complexed with 2-(4-hydroxyphenyl)-6-hydroxybenzo-β-thienyl-3-yl (4-carboxyphenyl)methanone, said crystal belonging to the space group P4122 and having the unit cell dimensions a=67.9 Å, b=67.9 Å, c=148.62 Å, and α=β=γ=90°, said crystal having the protein sequence of SEQ ID NO:2.

12. The crystal of claim 11, wherein said crystal has a resolution determined by X-ray crystallography of less than 3.5 Å.

13. The crystal of claim 11, comprising a binding pocket defined by the structure coordinates of human ERβ ligand binding domain amino acid residues $Met_{252}$, $Leu_{255}$, $Leu_{258}$, $Ala_{259}$, $Glu_{262}$, $Met_{293}$, $Leu_{296}$, $Met_{297}$, $Leu_{300}$, $Arg_{303}$, $Phe_{313}$, $Ile_{330}$, $Ile_{333}$, $Phe_{334}$, $Leu_{337}$, $Gly_{429}$, $His_{432}$, and $Leu_{433}$.

14. The crystal of claim 11, comprising a binding pocket defined by the structure coordinates of human ERβ ligand binding domain amino acid residues $Met_{252}$, $Leu_{255}$, $Thr_{256}$, $Leu_{258}$, $Ala_{259}$, $Asp_{260}$, $Glu_{262}$, $Leu_{263}$, $Trp_{292}$, $Met_{293}$, $Leu_{296}$, $Met_{297}$, $Gly_{299}$, $Leu_{300}$, $Arg_{303}$, $Phe_{313}$, $Gly_{329}$, $Ile_{330}$, $Ile_{333}$, $Phe_{334}$, $Leu_{337}$, $Lys_{428}$, $Gly_{429}$, $Met_{430}$, $Glu_{431}$, $His_{432}$, $Leu_{433}$, $Leu_{434}$, $Met_{436}$, $Val_{441}$, and $Val_{444}$.

15. A process of preparing a crystal of claim 11, comprising the steps of providing ERβ ligand binding domain complexed with 2-(4-hydroxyphenyl)-6-hydroxybenzo-β-thienyl-3-yl (4-carboxyphenyl)methanone, and growing one or more of said crystals by vapor diffusion.

* * * * *

SEQUENCE LISTING

<160> NUMBER OF SEQ ID NOS: 2

<210> SEQ ID NO: 1
<211> LENGTH: 229
<212> TYPE: PRT
<213> ORGANISM: Human

<400> SEQUENCE: 1

```
Asp Ala Leu Ser Pro Glu Gln Leu Val Leu Thr Leu Leu Glu Ala Glu
 1               5                  10                  15

Pro Pro His Val Leu Ile Ser Arg Pro Ser Ala Ser Met Met Met Ser
                20                  25                  30

Leu Thr Lys Leu Ala Asp Lys Glu Leu Val His Met Ile Ser Trp Ala
            35                  40                  45

Lys Lys Ile Pro Gly Phe Val Glu Leu Ser Leu Phe Asp Gln Val Arg
    50                  55                  60

Leu Leu Glu Ser Cys Trp Met Glu Val Leu Met Met Gly Leu Met Trp
65                  70                  75                  80

Arg Ser Ile Asp His Pro Gly Lys Leu Ile Phe Ala Pro Asp Leu Val
                85                  90                  95

Leu Asp Arg Asp Glu Gly Lys Cys Val Glu Gly Ile Leu Glu Ile Phe
            100                 105                 110

Asp Met Leu Leu Ala Thr Thr Ser Arg Phe Arg Glu Leu Lys Leu Gln
        115                 120                 125

His Lys Glu Tyr Leu Cys Val Lys Ala Met Ile Leu Leu Asn Ser Ser
    130                 135                 140

Met Tyr Pro Leu Val Asp Ser Ser Arg Lys Leu Ala His Leu Leu Asn
145                 150                 155                 160

Ala Val Thr Asp Ala Leu Val Trp Val Ile Ala Lys Ser Gly Ile Ser
                165                 170                 175

Ser Gln Gln Gln Ser Met Arg Leu Ala Asn Leu Leu Met Leu Leu Ser
            180                 185                 190
```

His Val Arg His Ala Ser Asn Lys Gly Met Glu His Leu Leu Met Met
        195                 200                 205

Lys Cys Lys Asn Val Val Pro Val Tyr Asp Leu Leu Leu Glu Met Leu
        210                 215                 220

Asn Ala His Val Leu
225

<210> SEQ ID NO: 2
<211> LENGTH: 228
<212> TYPE: PRT
<213> ORGANISM: Rat

<400> SEQUENCE: 2

Thr Leu Ser Pro Glu Gln Leu Val Leu Thr Leu Leu Glu Ala Glu Pro
1               5                   10                  15

Pro Asn Val Leu Val Ser Arg Pro Ser Met Pro Phe Thr Glu Ala Ser
        20                  25                  30

Met Met Met Ser Leu Thr Lys Leu Ala Asp Lys Glu Leu Val His Met
        35                  40                  45

Ile Gly Trp Ala Lys Lys Ile Pro Gly Phe Val Glu Leu Ser Leu Leu
    50                  55                  60

Asp Gln Val Arg Leu Leu Glu Ser Cys Trp Met Glu Val Leu Met Val
65                  70                  75                  80

Gly Leu Met Trp Arg Ser Ile Asp His Pro Gly Lys Leu Ile Phe Ala
                85                  90                  95

Pro Asp Leu Val Leu Asp Arg Asp Glu Gly Lys Cys Val Glu Gly Ile
            100                 105                 110

Leu Glu Ile Phe Asp Met Leu Leu Ala Thr Thr Ser Arg Phe Arg Glu
        115                 120                 125

Leu Lys Leu Gln His Lys Glu Tyr Leu Cys Val Lys Ala Met Ile Leu
        130                 135                 140

Leu Asn Ser Ser Met Tyr Pro Leu Ala Ser Ala Asn Gln Glu Ala Glu
145                 150                 155                 160

Ser Ser Arg Lys Leu Thr His Leu Leu Asn Ala Val Thr Asp Ala Leu
                165                 170                 175

Val Trp Val Ile Ala Lys Ser Gly Ile Ser Ser Gln Gln Gln Ser Val
            180                 185                 190

Arg Leu Ala Asn Leu Leu Met Leu Leu Ser His Val Arg His Ile Ser
        195                 200                 205

Asn Lys Gly Met Glu His Leu Leu Ser Met Lys Asp Leu Leu Leu Glu
        210                 215                 220

Met Leu Asn Ala
225